US008099300B2

(12) United States Patent
Gourley

(10) Patent No.: US 8,099,300 B2
(45) Date of Patent: *Jan. 17, 2012

(54) METHOD AND APPARATUS FOR PROCESSING PHARMACEUTICAL ORDERS TO DETERMINE WHETHER A BUYER OF PHARMACEUTICALS QUALIFIES FOR AN "OWN USE" DISCOUNT

(75) Inventor: Ewing B. Gourley, Springfield, MO (US)

(73) Assignee: Ewing B. Gourley, Springfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/641,644

(22) Filed: Dec. 18, 2009

(65) Prior Publication Data
US 2010/0100393 A1 Apr. 22, 2010

Related U.S. Application Data

(63) Continuation of application No. 09/710,227, filed on Nov. 10, 2000, now Pat. No. 7,640,170.

(51) Int. Cl.
*G06F 19/00* (2006.01)
(52) U.S. Cl. ...................... 705/2; 705/3; 705/1
(58) Field of Classification Search .................... 705/2–3
See application file for complete search history.

(56) References Cited

U.S. PATENT DOCUMENTS
5,890,129 A * 3/1999 Spurgeon ........................ 705/4
6,003,006 A * 12/1999 Colella et al. .................... 705/2
7,640,170 B1 12/2009 Gourley

OTHER PUBLICATIONS

Gardner, Jerome Richard, "Pharmaceutical Scam: Use Audit to Detect 'Pyramid Cube Scheme'" Sep. 1982, Healthcare Financial Management (HFM), vol. 36, No. 9, pp. 72, 74.*
"A Listing of Vendors and Suppliers of Computer Systems and Related Services for Retail Pharmacies", downloaded from http://www.computertalk.com/VendorLists_HTML/retl_all.shtml on Oct. 31, 2000, 19 pages.
"Focus on Sales and Marketing", E-commerce Pharmaceuticals, downloaded from http://www.streamingmedia.net/ecpharma/briefing041400.html on Sep. 29, 2000, pp. 1-4.

(Continued)

*Primary Examiner* — Robert Morgan
*Assistant Examiner* — Rachel L Porter
(74) *Attorney, Agent, or Firm* — Thompson Coburn LLP

(57) ABSTRACT

Disclosed is a method and apparatus for processing pharmaceutical orders to determine whether a buyer of pharmaceuticals qualifies for an "own use" discount. "Own use" discounts on pharmaceuticals are available for a limited class of buyers under 35 U.S.C. §13c. Under one method, an auditor receives an order for a quantity of pharmaceuticals, receives a report associated with the order containing sufficient information therein to perform an audit on the order, and compares the information found in the order with the information found in the associated report to make a status determination as to whether a buyer qualifies for an "own use" discount. Preferably a second report containing additional audit information is received as well. The auditor can also audit the order by comparing the order to this additional information. If these comparisons result in a determination that the buyer does in fact qualify for an "own use" discount, the auditor can then place the order with a pharmaceutical seller for a discounted price. Also disclosed is a pharmaceutical order auditing system that uses a computer to perform the above-described audit.

20 Claims, 10 Drawing Sheets

OTHER PUBLICATIONS

"Welcome to the ComputerTalk Web Site . . . A Great Place to Shop for Healthcare Computer Systems and Software", downloaded from http://www.computertalk.com/FromMainFrame/home.html on Oct. 31, 2000, pp. 1-2.

*Abott Laboratories* v. *Portland Retail Druggists Associations, Inc.* 425 US 1, 47 L.Ed.2d 537, 96 S.Ct. 1305 (1976).

Amendment After Allowance for U.S. Appl. No. 09/710,227 dated Oct. 27, 2009.

Amendment and Response to Office Action for U.S. Appl. No. 09/710,227 dated Mar. 14, 2006.

Amendment and Response to Office Action for U.S. Appl. No. 09/710,227 dated Apr. 28, 2009.

Amendment and Response to Restriction Requirement for U.S. Appl. No. 09/710,227 dated Nov. 2, 2004.

Appeal Brief for U.S. Appl. No. 09/710,227 dated Feb. 14, 2008.

Examiner's Answer for U.S. Appl. No. 09/710,227 dated May 2, 2008.

Examiner's Answer for U.S. Appl. No. 09/710,227 dated Sep. 18, 2008.

Gardner, Jerome Richard, "Pharmaceutical Scam: Use Audit to Detect 'Pyramid Cube Scheme'" Sep. 1982, Healthcare Financial Management (HFM), vol. 36, No. 9, pp. 72, 74.

Gire, Michael K., "Hospital Procurement and Illegal Price Discrimination," Nov. 1989, Hospital Material Management Quarterly, vol. 11, No. 2, pp. 71-76.

*GTE Products Corporation* v. *Broadway Electrical Supply Co., Inc.*, 676 N.E. 2d 1151, 42 Mass. App. Ct. 293 (1997).

Health Resources USA, L.L.C. pamphlet, one page, uncirculated.

In re Brand Name Prescription Drugs Antitrust Litigation, 123 F.3d 599 (7th Cir. 1997).

In re Brand Name Prescription Drugs Antitrust Litigation, 186 F.3d 781 (7th Cir. 1999).

Interview Summary for U.S. Appl. No. 09/710,227 dated May 7, 2009.

Letter dated Jul. 13, 2000 from Health Resources USA, LLC to Drug Enforcement Administration, one page.

Letter dated Jul. 6, 2000 from Health Resources USA, LLC to Drug Enforcement Program, four pages.

Letter dated Jul. 7, 2000 from Drug Enforcement Program to Health Resources USA, LLC, one page.

Nielsen, Richard P., "Public Policy and Price Discrimination in Favor of Nonprofit and against Profit Seeking Organizations," Apr. 1977, The Academy of Management Review, vol. 2, No. 2, pp. 316-319.

Notice of Allowance for U.S. Appl. No. 09/710,227 dated Aug. 24, 2009.

Office Action for U.S. Appl. No. 09/710,227 dated Jan. 29, 2009.
Office Action for U.S. Appl. No. 09/710,227 dated Jul. 28, 2006.
Office Action for U.S. Appl. No. 09/710,227 dated Mar. 10, 2005.
Office Action for U.S. Appl. No. 09/710,227 dated Nov. 14, 2005.
Office Action for U.S. Appl. No. 09/710,227 dated Oct. 4, 2004.
Reply Brief for U.S. Appl. No. 09/710,227 dated Jul. 1, 2008.
Reply Brief for U.S. Appl. No. 09/710,227 dated Oct. 30, 2008.
Response to Rule 105 Communication for U.S. Appl. No. 09/710,227 dated May 10, 2005.
Response to Rule 312 Communication for U.S. Appl. No. 09/710,227 dated Nov. 12, 2009.
U.S. v. Ferro, No. 00-2467 (8th Cir. 2001), pp. 1-6.

* cited by examiner

RETAIL PHARMACY A

NURSING HOME Z: PROZAC
9/1/2000-9/30/2000

| REPORT SUMMARY | #RX | NEW | REFILLS | AMOUNT |
|---|---|---|---|---|
| REPORT TOTALS | 8 | 1 | 7 | 420 |
| NEW RX TOTALS | 1 | 1 |  | 30 |
| REFILL TOTALS | 7 |  | 7 | 390 |

PATIENTS: JOHN SMITH, JOHN DOE, JOHN JOHNSON, JOHN JONES, JANE SMITH, JANE DOE, JANE JOHNSON, JANE JONES

FIG. 2A

RETAIL PHARMACY B

NURSING HOME Y: PROZAC
9/1/2000-9/30/2000

| REPORT SUMMARY | #RX | NEW | REFILLS | AMOUNT |
|---|---|---|---|---|
| REPORT TOTALS | 4 | 2 | 2 | 80 |
| NEW RX TOTALS | 2 | 2 |  | 30 |
| REFILL TOTALS | 2 |  | 2 | 50 |

PATIENTS: BILL SMITH, BRIAN JOHNSON, MARY JONES, MARTHA ADAMS

FIG. 2B

| PHYSICIANS ORDER SHEET | | |
|---|---|---|
| FACILITY: NURSING HOME Z | | |
| ORDER REVIEWED BY: NURSE SMITH (117) | | DATE REVIEWED: 9/30/2000 |
| MEDICATIONS (170) | HRS. (172) | PHYSICIANS ORDERS (174) |
| PROZAC 20 mg TAB —ONE TABLET BY MOUTH DAILY 6/10/2000 (175) | 6 AM | DIET: NO CONCENTRATED SWEETS *HYPERTENSION FOUND |
| PREVACID 15 mg CAP —TWO CAPS BY MOOUTH DAILY 6/10/2000 (175) | 7 AM | |
| PAXIL 20 mg TAB —ONE TAB BY MOUTH DAILY 6/10/2000 (175) | 9 AM | RECAPPED: 9/30 NURSE SMITH, RN (177) |
| | | PHARMACIST REVIEW COMPLETED:<br>☐ NO APPARENT IRREGULARITIES FOUND<br>☐ REFER TO CONSULTANT REVIEW FORM<br>SIGNATURE: _____ DATE: _____ |
| | | FROM: 9/1/2000 THRU 9/30/2000 |
| | | ATTENDING PHYSICIAN: DR. JONES (179)<br>SIGNATURE: *Dr. Jones* DATE: 9/30/2000 |
| | | GENERIC EQUIVALENTS MAY BE USED UNLESS THE ORDER IS SPECIFICALLY FOLLOWED BY THE NOTATION: USE NO SUBSTITUTES |
| | | PATIENT: PATIENT 1 MEDICAID #:___<br>ADMIST #: ___ MEDICARE #: ___<br>ADMIT DATE: ___ AGE:___ SEX ___<br>BIRTH DATE: ___ |

FIG. 3

| SIGNATURE | INITIALS | SIGNATURE | | | | | | | INITIALS | SIGNATURE | | | | | | | INITIALS | MEDICATION ADMINISTRATION RECORD | | | | | | | | | | | | | | |
|---|---|---|---|---|---|---|---|---|---|---|---|---|---|---|---|---|---|---|---|---|---|---|---|---|---|---|---|---|---|---|---|---|
| 176 | 178 | NURSE SMITH | | | | | | | N.S. | NURSE JONES | | | | | | | N.J. | 180 | | | | | | | | | | | | | | |
| MEDICATIONS | HOURS | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
| PROZAC 20 mg DAILY | 6 AM | x | x | x | x | x | x | x | x | x | x | x | x | x | x | x | x | x | x | x | x | x | x | x | x | x | x | x | x | x | x | x |
| PREVACID 15 mg DAILY (2X) | 7 AM | x | x | x | x | x | x | x | x | x | x | x | x | x | x | x | x | x | x | x | x | x | x | x | x | x | x | x | x | x | x | x |
| PAXIL 20 mg DAILY | 9 AM | x | x | x | x | x | x | x | x | x | x | x | x | x | x | x | x | x | x | x | x | x | x | x | x | x | x | x | x | x | x | x |

PATIENT INFO: NAME: PATIENT 1   ADMIT #: ___   DIET: ___
NURSING HOME: NURSING HOME Z   9/1/2000 THRU 9/30/2000
ROOM #: ___
ADMIT DATE: ___

METHOD AND APPARATUS FOR PROCESSING PHARMACEUTICAL ORDERS TO DETERMINE WHETHER A BUYER OF PHARMACEUTICALS QUALIFIES FOR AN "OWN USE" DISCOUNT

CROSS-REFERENCE AND PRIORITY CLAIM TO RELATED APPLICATION

This application is a continuation application of U.S. application Ser. No. 09/710,227, filed on Nov. 10, 2000, and entitled METHOD AND APPARATUS FOR PROCESSING PHARMACEUTICAL ORDERS TO DETERMINE WHETHER A BUYER OF PHARMACEUTICALS QUALIFIES FOR AN "OWN USE" DISCOUNT, now U.S. Pat. No. 7,640,170, the entire disclosure of which is incorporated by reference herein.

BACKGROUND OF THE INVENTION

The Robinson-Patman Price Discrimination Act, 15 USC §13(a), generally makes it unlawful for one engaged in commerce to discriminate in price between different purchasers of like commodities where, among other things, "the effect of such discrimination may be substantially to lessen competition." *Abbott Laboratories v. Portland Retail Druggists Association,* 425 U.S. 1, 3-4, 47 L. Ed. 2d 537, 543 (1976). This United States law essentially prevents pharmaceutical sellers from selling a given type of pharmaceutical at regular price to one buyer and then selling that same type of pharmaceutical at a discounted price to another buyer. However, an exception to the Robinson-Patman Act exists stating that "nothing in the [Robinson-Patman Act], shall apply to purchases of their supplies for their own use by schools, colleges, universities, public libraries, churches, hospitals, and charitable institutions not operated for profit." 15 USC §13c. Because of this exception, hospitals, nursing homes, long term health care facilities, and the like are eligible for purchasing pharmaceuticals at a discounted price—an "own use" discount—when they are buying pharmaceuticals on behalf of their patients or in some situations, their employees. Therefore, when nursing homes purchase pharmaceuticals on behalf of their patients, they are eligible to purchase such pharmaceuticals from the pharmaceutical manufacturer at a discounted price.

However, nursing homes, as with most other pharmaceutical buyers, do not buy their pharmaceuticals directly from the pharmaceutical manufacturer. Rather, they purchase their pharmaceuticals through a distributor who buys large quantities of pharmaceuticals, stores those large quantities, and distributes them to various buyers upon request. Pharmaceutical sellers are reluctant to sell discounted pharmaceuticals to distributors because of a fear that the distributor will buy more discounted pharmaceuticals than necessary to supply the distributor's "own use"-eligible customers, and then sell the surplus to customers not eligible for an "own use" discount (thereby pocketing fraudulently-obtained profits). Pharmaceutical manufacturers call this practice "diversion" and understandably dislike it.

One system currently in place that is used by pharmaceutical manufacturers to prevent "diversion" of "own use" discount pharmaceuticals is a "chargeback" or "rebate" system. See *In re Brand Name Prescription Drugs Antitrust Litigation,* 186 F.3d 781, 783-4 (7th Cir. 1999). In this chargeback/rebate system, the pharmaceutical manufacturer sells pharmaceuticals to a distributor at a regular price. The pharmaceutical manufacturer then contracts directly with "own use"-eligible buyers for a discounted price. If the "own use"-eligible buyer then buys pharmaceuticals from a distributor at that discounted price, the pharmaceutical manufacturer will reimburse the distributor (provide a rebate) for the difference between the regular price and the discounted price. To obtain this rebate, the distributor must make a representation to the pharmaceutical manufacturer that the discount was given to the "own use"-eligible buyer. FIG. 1 depicts a diagram for this chargeback system. The chargeback or rebate system obviously requires both the manufacturer and the distributor to maintain a dual set of accounting and disbursement records which results in increased overhead for both parties. The rebate system is designed primarily around "own use" purchasers such as hospital pharmacies, closed pharmacies, and health maintenance organizations. Because of the single, non-retail focus of these organizations, manufacturers and distributors assume that their orders of pharmaceuticals are true "own use" orders. However, the opportunity for diversion does exist as many of these purchasers, such as hospitals and HMOs have retail pharmacy outlets where "own use" pharmaceuticals could be directed, and the rebate system provides virtually no policing to determine whether or not the diversion actually occurs.

Currently, in the United States, according to a report by the SMG Marketing Group of Chicago, Ill., approximately 55% of nursing homes purchase their pharmaceuticals from "closed pharmacies." A closed pharmacy is a pharmacy that supplies pharmaceuticals to institutions such as hospitals or nursing homes, but does not sell pharmaceuticals to walk-in customers. Because these closed pharmacies have an exclusive customer list of customers who are eligible to buy pharmaceuticals at an "own use" discount, pharmaceutical manufacturers are willing to sell pharmaceuticals to these closed pharmacies at a discounted price. That is, pharmaceutical manufacturers are not overly worried that the "closed pharmacy" will sell discounted pharmaceuticals at a regular price to customers ineligible for a discount, because the "closed pharmacy" has virtually no such customers.

However, approximately 45% of nursing homes are served by retail pharmacies. These retail pharmacies, in addition to supplying the pharmaceutical needs of a nursing home, also supply pharmaceuticals to walk-in customers. Thus, when a retail pharmacy purchases drugs from a pharmaceutical manufacturer or a pharmaceutical distributor, the retail pharmacy may be purchasing pharmaceuticals on behalf of not only the nursing home, but also its walk-in customer trade. Because these retail pharmacies are supplying pharmaceuticals to walk-in customers as well as nursing homes, pharmaceutical manufacturers have been unwilling to sell "own use" discount pharmaceuticals to such retail pharmacies for fear of diversion. That is, the pharmaceutical manufacturer is afraid that the retail pharmacy will commingle its "own use" discount pharmaceuticals with its walk-in customer pharmaceuticals. To date, retail pharmacies have been unable to obtain "own use" discounts when buying pharmaceuticals on behalf of nursing homes. As a result, some 7,648 nursing homes (approximately 45% of all nursing homes) pay more money than necessary when purchasing pharmaceuticals.

Not helping the retail pharmacy in this quest for an "own use" discount on pharmaceuticals purchased on behalf of a nursing home is the limited market power that each individual retail pharmacy possesses in relation to the pharmaceutical manufacturer. To improve their buying power, retail pharmacies have banded together to form buying groups, or buyers co-ops. These buyers co-ops can amass several orders from each retail pharmacy which belongs to the buyers co-op. Armed with a large order for a given type of pharmaceutical, the buyers co-op has some negotiation power with the pharmaceutical manufacturer to obtain a discounted price. However, before the pharmaceutical manufacturer is willing to sell these pharmaceuticals at a discounted price, the pharmaceutical seller still needs assurances that such discounted pharmaceuticals are actually being used by institutions eligible for an "own use" discount. Because no system currently in place has adequately assured pharmaceutical manufacturers that the buyers co-ops or retail pharmacies are not diverting "own use" discounted pharmaceuticals, nursing homes that are supplied with pharmaceuticals by a retail pharmacy continue to be unable to purchase "own use" discount pharmaceuticals. This inability to purchase discounted pharmaceuticals leads to nursing homes having higher operational costs, costs which are passed down to nursing home residents who end up paying a higher price than necessary to reside in such nursing homes.

SUMMARY OF THE INVENTION

The inventors herein have developed a method and apparatus for bringing the "own use" discount to retail pharmacies when those retail pharmacies are purchasing pharmaceuticals on behalf of a nursing home.

In one aspect of the invention, a method is provided for processing orders for "own use" discount pharmaceuticals comprising the steps of receiving an order comprising a request from a buyer for a quantity of a type of pharmaceutical, receiving an associated report summarizing the "own use" pharmaceutical needs of at least one patient who is supplied with pharmaceuticals by the buyer, comparing the order with the associated report, and if the associated report supports the order, then making a status determination that the buyer qualifies for purchasing the quantity of the type of pharmaceutical ordered at a price reduced by an "own use" discount. The order may be received electronically on a computer as a transmission over the Internet. The associated report may also be received electronically as at least one computer file. A computer can then be used to perform the comparison between the order and the associated report. The method may further comprise converting the at least one computer file containing the associated report to a format readable by the computer making the comparison. Such a step is necessary when the received computer file has a data format that cannot be read by the comparison computer absent a conversion. Alternatively, the information contained in the associated report can be entered as data into the computer if necessary. Also, the information in the order can be entered as data into the computer if necessary.

The method further provides for receiving a second associated report summarizing the "own use" pharmaceutical needs of at least one patient who is supplied with pharmaceuticals by the buyer, comparing the second associated report with either the order or the first associated report, wherein the status determination further depends upon whether the second associated report supports the information against which it was compared. As with the first associated report, the second associated report may also be received electronically as at least one computer file. A computer can be used to perform the comparison. Also, the method may further provide for converting the at least one computer file containing the second associated report to a format readable by the computer making the comparison. As previously explained, such a step is necessary when the received computer file has a data format that cannot be read by the comparison computer absent a conversion. Alternatively, the information in the associated report can be entered as data into the computer.

The method of the present invention may further provide for placing the order with a pharmaceutical seller if the status determination identifies the buyer as qualified for the "own use" discount. This order will have a price reduced by the "own use" discount. The method may further comprise sending either the first associated report or the second associated report, or both reports, to the pharmaceutical seller. Also, the method may further comprise allowing the pharmaceutical seller to have access to either the first associated report or the second associated report, or both reports. Further still, a status report can be generated and sent to the pharmaceutical seller.

The buyer may be an entity comprised of at least one retail pharmacy supplying pharmaceuticals to at least one nursing home, the at least one nursing home having at least one patient needing the type of pharmaceutical ordered. Alternatively, the buyer may be at least one retail pharmacy supplying pharmaceuticals to at least one nursing home, the at least one nursing home having at least one patient needing the type of pharmaceutical ordered.

The method of the present invention may further provide for arranging for the pharmaceutical seller to directly ship (plant deliver) an appropriate quantity of the type of pharmaceutical ordered to an entity comprised of at least one retail pharmacy supplying pharmaceuticals to at least one nursing home, the at least one nursing home having at least one patient needing the type of pharmaceutical ordered, or directly ship (plant deliver) an appropriate quantity of the type of pharmaceutical ordered to at least one retail pharmacy supplying pharmaceuticals to at least one nursing home, the at least one nursing home having at least one patient needing the type of pharmaceutical ordered, or directly ship (plant deliver) an appropriate quantity of the type of pharmaceutical ordered to at least one nursing home having at least one patient needing the type of pharmaceutical ordered.

Further still, if an order does not qualify for an "own use" discount because, for example, the quantity ordered is not supported by the audit material, the method of the present invention may provide for adjusting an order so that the order, as adjusted, will qualify for an "own use" discount. In making this adjustment, the method may provide for calculating a stand-by requirement for the buyer.

Either the first or second associated report can be a listing compiled by each of the retail pharmacies requesting pharmaceuticals. These listings contain a record of pharmaceuticals requested by each nursing home to which the retail pharmacies supply pharmaceuticals. Also, the first or second associated report can be a physicians order sheet (POS) for each patient in each nursing home requesting an amount of pharmaceuticals. Further still, the first or second associated report can be a medication administration record (MAR) for each patient in each nursing home requesting an amount of pharmaceuticals.

In another aspect of the invention, a pharmaceutical order auditing system for determining whether a pharmaceutical buyer qualifies for an "own use" discount is provided. The pharmaceutical order auditing system comprises a first input for receiving pharmaceutical order data comprising a type of pharmaceutical, a quantity that type of pharmaceutical, and a buyer requesting that quantity of that type of pharmaceutical, a second input for receiving audit data that is sufficient for a status determination of whether the buyer qualifies for purchasing the quantity at a price reduced by an "own use" discount, software configured to compare the order data with the audit data to make a status determination whether the buyer qualifies for purchasing the quantity at a reduced price, the status determination depending upon the comparison, and an output for communicating the status determination to a user.

Preferably, the pharmaceutical order auditing system further comprises a third input for receiving additional audit data that is sufficient for a status determination of whether the buyer qualifies for purchasing the quantity at a price reduced by an "own use" discount. The software is then further configured to compare the additional audit data with either the order data or the audit data in making the status determination.

The audit data and additional audit data may identify the type of pharmaceutical requested, the amount of pharmaceutical requested, and the names of the nursing homes making the request. Additionally, the order data, audit data, and additional audit data may identify the patients needing the pharmaceuticals in the order. If a sufficient correlation exists between these types of data, the software can make a status determination verifying the buyer's eligibility for the "own use" discount. As previously explained, the audit data and the additional audit data can be gathered from any of the following: retail pharmacy listings, physicians order sheets, or medication administration records. Preferably, the audit data and additional audit data is received electronically. Converters can be used to convert the data to a common format if necessary. Alternatively, the data can be entered into a computer.

The software can be configured to allow for a tolerance in making the status determination when an amount of the type of pharmaceutical requested by either a retail pharmacy or a nursing home does not match a package amount offered by the pharmaceutical seller. The software can also be configured to adjust an order so that the order, as adjusted, will qualify for an "own use" discount. Such an adjustment may be needed if an order does not qualify for an "own use" discount because, for example, the quantity ordered is not supported by the audit material. In making this adjustment, the software can be configured to calculate a stand-by requirement for the buyer. Also, the output can be communicated to the user in the form of a status report.

In yet another aspect of the present invention, a method is disclosed for providing "own use" discount pharmaceuticals to buyers that qualify for an "own use" discount. This method comprises receiving an order from a buyer for a quantity of a type of pharmaceutical, receiving an associated report summarizing the "own use" pharmaceutical needs of at least one patient who is supplied with pharmaceuticals by the buyer, placing the order with a pharmaceutical seller at a price reduced by the discount, and making the associated report available to the pharmaceutical seller. The method may further provide for receiving a second associated report summarizing the "own use" pharmaceutical needs of at least one patient who is supplied with pharmaceuticals by the buyer and making the second associated report available to the pharmaceutical seller.

In yet another aspect of the present invention, a method is disclosed for providing "own use" discount pharmaceuticals to buyers that qualify for an "own use" discount. This method comprises receiving an order from a buyer for a quantity of a type of pharmaceutical, receiving an associated report summarizing the "own use" pharmaceutical needs of at least one patient who is supplied with pharmaceuticals by the buyer, placing the order with a pharmaceutical seller at a price reduced by the discount, and sending the associated report to the pharmaceutical seller. The method may further provide for receiving a second associated report summarizing the "own use" pharmaceutical needs of at least one patient who is supplied with pharmaceuticals by the buyer and sending the second associated report to the pharmaceutical seller.

By implementing a methodology for verifying whether a pharmaceutical buyer does in fact qualify for an "own use" discount, the present invention enables nursing homes that purchase pharmaceuticals from retail pharmacies to purchase those pharmaceuticals at a discounted price. The practice of the present invention will assure pharmaceutical sellers that a buyer is not diverting discount purchases because the present invention verifies that there is an "own use"-eligible institution and consumer on the receiving end of the order. This "customer direct" discount enables a nursing home to administer discounted pharmaceuticals to its patients when those patients have selected a supplying pharmacy that the nursing home has approved, and the supplying pharmacy has been found to qualify for an "own use" discount. These and other features and advantages of the method an apparatus of the present invention will be in part apparent, and in part pointed out hereinafter.

BRIEF DESCRIPTION OF THE DRAWINGS

FIGS. 2a and 2b illustrate examples of listings maintained by retail pharmacies that track pharmaceuticals supplied to customers.

FIG. 3 depicts an example of a physicians order sheet (POS) maintained by nursing homes.

FIG. 4 depicts an example of a medication administration record (MAR) maintained by nursing homes.

DETAILED DESCRIPTION OF THE PREFERRED EMBODIMENT

Figure 1:
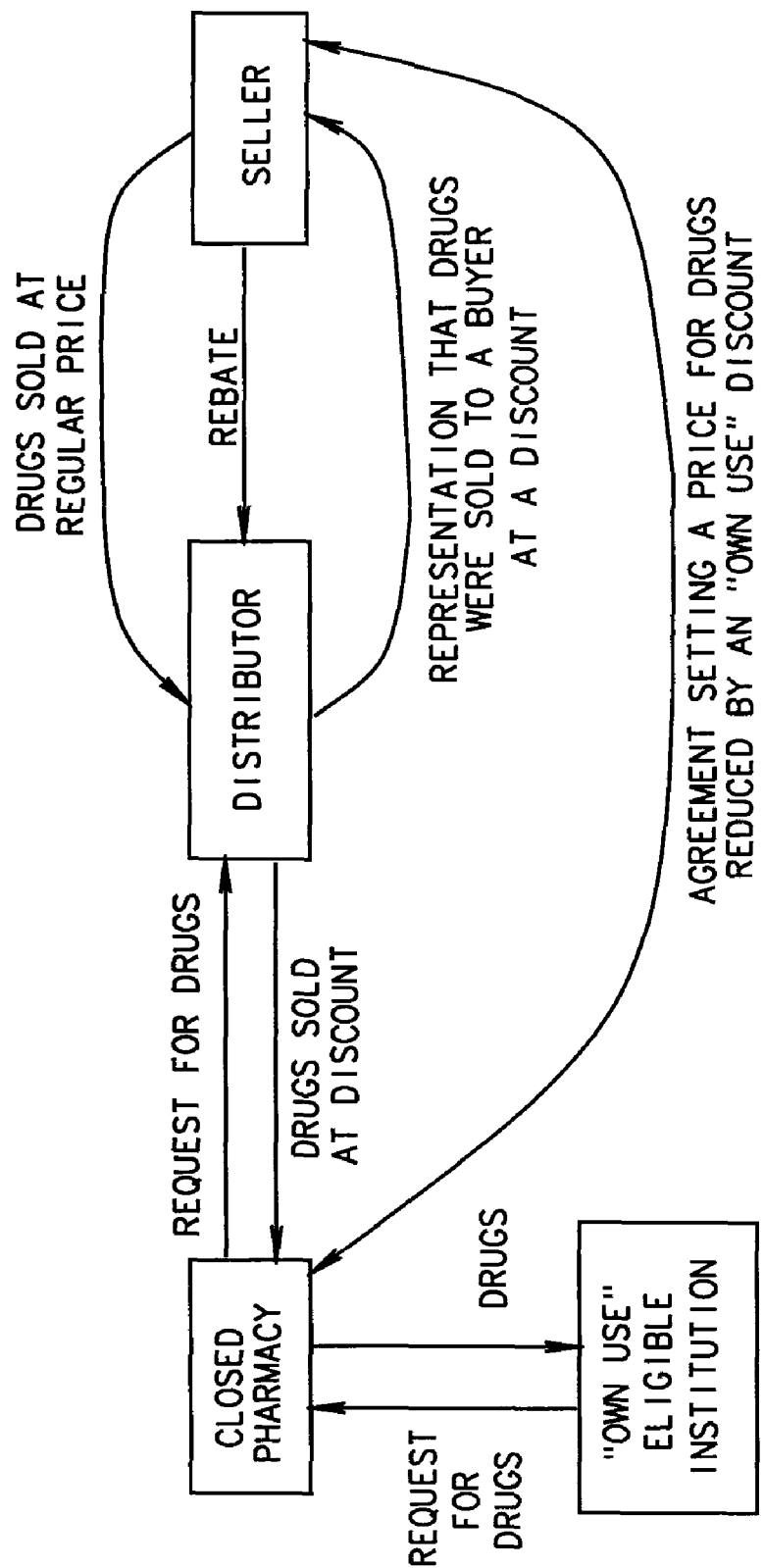
FIG. 1 illustrates the chargeback system currently in place between pharmaceutical manufacturers, pharmaceutical distributors, and "own use" discount buyers.

The present invention will first be explained in terms of the information that needs to be obtained to perform a sufficient audit on an order when making a status determination as to whether the buyer qualifies for purchasing pharmaceuticals at a price reduced by an "own use" discount. Obtaining the proper information is an important aspect of the present invention. To properly perform an "own use" audit, one must be able to compare a quantity of a given type of pharmaceuticals requested in an order with information evidencing that an "own use"-eligible institution actually needs the quantity of the type of pharmaceutical requested. Thus, any report used to audit an order for "own use" discount pharmaceuticals should summarize the "own use" pharmaceutical needs of at least one patient in an "own use"-eligible institution.

This information can be obtained from a variety of sources. For example, retail pharmacies maintain computerized records of the pharmaceuticals that they supply to customers. Thus, each retail pharmacy is capable of generating a listing identifying the type and amount of pharmaceuticals given to each nursing home to which it supplies pharmaceuticals. These listings can have a varying degree of detail. For example, FIG. 2(a) shows an example of a listing 166 that can be generated by a retail pharmacy. As can be seen, this listing was compiled by Retail Pharmacy A. It identifies the amount of Prozac requested by Nursing Home Z from Sep. 1, 2000 to Sep. 30, 2000. Column 150 contains a record of the number of prescriptions requested by the nursing home during the time indicated. Column 152 contains a record of the number of new prescriptions that were requested during the indicated time period. Column 154 contains a record of the number of prescriptions that were refilled by the retail pharmacy during the time period indicated. Column 156 identifies the amount of Prozac requested over the indicated time period. Rows 158, 160, and 162 identify the listing totals, new prescription totals, and refill prescription totals respectively. Additionally, this listing may also contain a patient list 164 identifying the patients in Nursing Home Z whose prescriptions are covered by the listing. This patient list can either identify the patients by name, or by other means such as an ID number (if necessary for confidentiality reasons). In this example, it can be seen that 8 total prescriptions of Prozac were filled by Retail Pharmacy A on behalf of Nursing Home Z from Sep. 1, 2000 to Sep. 30, 2000. The fact that 8 prescriptions were filled means that 8 patients at Nursing Home Z need Prozac. This number can also be verified by counting the number of patients identified in patient list 164. Of these 8 prescriptions, one is a new prescription, and seven are refills of old prescriptions. To meet the request for 8 prescriptions, it can be seen that an amount of 420 pills of Prozac are needed.

FIG. 2(*b*) depicts an example of a listing that can be generated by Retail Pharmacy B identifying the amount of Prozac requested by Nursing Home Y from Sep. 1, 2000 to Sep. 30, 2000. The rows and columns contain the same types of information as those in the listing of FIG. 2(*a*). In this example, it can be seen that 4 total prescriptions of Prozac were filled by Retail Pharmacy B on behalf of Nursing Home Y from Sep. 1, 2000 to Sep. 30, 2000. Thus, 4 patients in Nursing Home Y needed Prozac, and these patients can be identified in patient list 164. The total amount of Prozac needed to fill these prescriptions is identified as 80 pills.

Thus, if Retail Pharmacy A and Retail Pharmacy B belong to the same buyers co-op, they could pool their requests together to assemble an order for 500 pills of Prozac. Because nursing homes are to receive that 500 pill quantity, the order is eligible for an "own use" discount. To verify that the 500 pill order is in fact destined for an "own use" eligible facility, the buyers co-op, when placing its order, would also forward a report consisting of each listing maintained by Retail Pharmacy A and Retail Pharmacy B associated with the order so that an audit can be performed on that order.

The retail pharmacy listings depicted in FIGS. 2(*a*) and 2(*b*) can be generated with existing software used by retail pharmacy computers. This software is capable of generating a nursing home-specific report for various pharmaceuticals supplied by the retail pharmacy to a nursing home over a desired time period. Yet another example of retail pharmacy listings that can be used in the practice of the present invention are the electronic billing statements that retail pharmacies provide to state Medicaid departments. These electronic billing statements contain a record of pharmaceuticals supplied to patients in a nursing home that are on Medicaid.

Another source for audit information are the records kept by nursing homes that detail the amount and type of pharmaceuticals that the nursing home administers to its patients. For example, nursing homes maintain a physicians order sheet (POS) for each patient in the nursing home. The POS contains a monthly record of the pharmaceuticals administered and prescribed to a given patient. FIG. 3 depicts a typical POS. As can be seen, this POS covers Patient 1 who is a resident of Nursing Home Z. The time period covered by this POS is Sep. 1, 2000 to Sep. 30, 2000, as can be seen in the lower right hand corner. Column 170 identifies the medications currently being taken by Patient 1. Column 172 identifies the time of day at which the medications are to be taken, and column 174 identifies any new diagnoses, treatments, or prescriptions that may be made by a doctor during the applicable time period. Each date 175 in the medication column 170 identifies the date on which the prescription for that medication was originally made. These records are typically reviewed for accuracy by nursing home personnel each month. The attending physician for Patient 1 signs the POS, as can be seen by signature 179. The nurse who reviews the POS for accuracy will sign the POS as well, as can be seen in nurse review notations 177.

In this POS, it can be seen that Patient 1 takes one 20 milligram tablet of Prozac, two 15 milligram capsules of Prevacid, and one 20 milligram tablet of Paxil each day. Thus, each month Patient 1 needs about 30 (or 31) pills of Prozac, 60 (or 62) pills of Prevacid and 30 (or 31) pills of Paxil. In relation to the retail pharmacy listing depicted in FIG. 2A, this POS would partially support Retail Pharmacy A's request for 420 pills of Prozac on behalf of Nursing Home Z. If Retail Pharmacy A obtains a POS for each patient in Nursing Home Z that takes Prozac, and these POSs establish that patients in Nursing Home Z need 420 pills of Prozac for the month, the retail pharmacy would be able to further prove that its request for 420 pills of Prozac qualifies for an "own use" discount.

Another record kept by nursing homes to track pharmaceuticals given to patients is the medication administration record (MAR). FIG. 4 depicts a typical MAR. The MAR is essentially an exploded POS that charts the medications given to a patient on a daily basis. Column 176 identifies the various pharmaceuticals to be given to the patient identified in box 182. Box 182 contains various patient information such as name, room number, dates of residence, etc. Column 178 identifies the time of day that each pharmaceutical listed in column 176 is to be given to the patient. Chart 180 has boxes for each day of the month and for each medication to be administered. Each box within chart 180 is x'ed or initialed by the nurse or doctor after the patient actually receives the listed medication.

In this MAR, it can be seen that Patient 1 takes one 20 milligram tablet of Prozac, two 15 milligram capsules of Prevacid, and one 20 milligram tablet of Paxil each day. Thus, each month, Patient 1 needs about 30 (or 31) pills of Prozac, 60 (or 62) pills of Prevacid, and 30 (or 31) pills of Paxil. As can be seen, this MAR is essentially duplicative of the POS shown in FIG. 3. Thus, it is easily understood that the POS and MAR can be used interchangeably as they are for the most part equivalent records. Like the POS of FIG. 3, this MAR would partially support Retail Pharmacy A's request for 420 pills of Prozac on behalf of Nursing Home Z. If Retail Pharmacy A obtains an MAR for each patient in Nursing Home Z that takes Prozac, and these MARS establish that patients in Nursing Home Z need 420 pills of Prozac for the month, then Retail Pharmacy A would be able to further prove that its request for an amount of 420 pills of Prozac qualifies for an "own use" discount.

Thus, for a retail pharmacy to establish that it is buying a given amount of pharmaceuticals on behalf of a nursing home, it can rely upon any of the above-described reports: the listings maintained in the records of the retail pharmacy itself, the POSs maintained by the nursing home for each patient receiving pharmaceuticals through the retail pharmacy, or the MARS maintained by the nursing home for each patient receiving pharmaceuticals through the retail pharmacy. While in the preferred embodiment of the present invention, the retail pharmacy listings and nursing home POSs are used to determine whether a retail pharmacy's request for an amount of pharmaceuticals qualifies for an "own use" discount, it should be easily understood that any, or all, of these reports can be used to support a retail pharmacy's request for "own use" discount pharmaceuticals.

Figure 5:
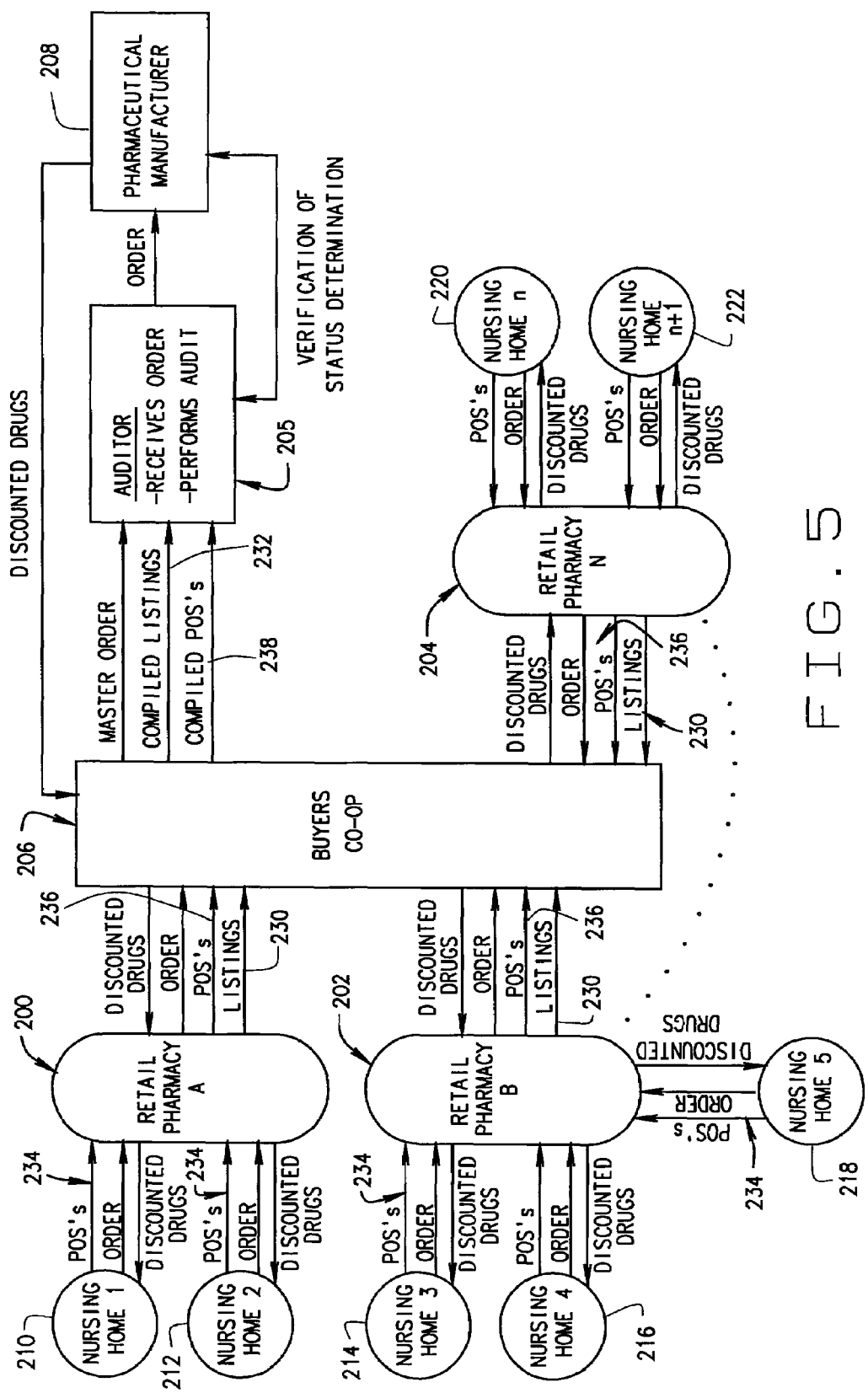
FIG. 5 depicts an overview of the preferred embodiment of the present invention.

FIG. 5 depicts an overview of the present invention. Circles 200, 202, and 204 identify the retail pharmacies that supply pharmaceuticals to nursing homes 210, 212, 214, 216, 218, 220, and 222. As can be seen, retail pharmacy 200 supplies pharmaceuticals to nursing homes 210 and 212. Retail pharmacy 202 supplies pharmaceuticals to nursing homes 214, 216, and 218, and retail pharmacy 204 supplies pharmaceuticals to nursing homes 220 and 222. Each retail pharmacy 200, 202, and 204 belong to a buyers co-op 206. The buyers co-op 206 may have numerous members who are retail pharmacies that supply pharmaceuticals to nursing homes, or it may have just a few. Also, it is highly likely that many members of the buyers co-op will be retail pharmacies that cater strictly to walk-in customers, and not to nursing homes. The buyers co-op 206 functions to amass each request for an amount of a given type of pharmaceutical from each of its retail pharmacy members into a master order. Because the quantity of pharmaceuticals in the buyers co-op order should be a large amount (the sum of amounts requested by each of the retail pharmacies 200, 202 and 204), the buyers co-op has "market power" that would allow it to negotiate with a pharmaceutical seller 208 for a favorable price. However, as previously discussed, because of the pharmaceutical seller's fear that the buyers co-op or retail pharmacy will divert some or all of the discounted drugs to its walk-in customer trade, pharmaceutical sellers have previously been unwilling to sell pharmaceuticals to buyers co-ops with retail pharmacy members, even when some of those retail pharmacies are purchasing pharmaceuticals on behalf of nursing homes.

The present invention involves having the buyers co-op 206 place its order with a practitioner 205 of the present invention (the practitioner of the present invention will hereinafter be referred to as an "auditor") so that an audit can be done on the order to determine whether the buyers co-op qualifies for an "own use" discount. However, it must be noted that it is within the scope of the invention for a retail pharmacy to place its order directly with the auditor, thus bypassing the buyers co-op. However, in most situations, it will be the buyers co-op that places the order. If the audit results in a determination that the buyers co-op does in fact qualify for an "own use" discount, the auditor 205 will essentially function as a "closed distributor" who places the co-op's order with a pharmaceutical seller at a discounted price. Alternatively, the auditor can act purely as an independent auditing agency who determines whether a buyer qualifies for an "own use" discount and reports its determination to interested parties without getting involved in placing any orders with a pharmaceutical seller. For example, a buyers co-op may place an order with a pharmaceutical seller wherein the buyers co-op requests a discounted price. Before the pharmaceutical manufacturer fills the order at the discounted price, it would employ the auditor to make a determination as to whether the buyer in fact qualifies for the discount. Under either implementation, a discounted price will be available because the auditor will be able to verify to the seller that the quantity of pharmaceuticals in the order are truly destined for nursing homes.

Once the "own use" discount is obtained, the auditor can arrange for the seller to directly ship the filled order to the co-op (this direct shipment is also known as a plant delivery). By having the order shipped directly to the co-op, the auditor will avoid any actual possession of the pharmaceuticals, which alleviates the need for the auditor to obtain DEA licensing under current federal laws. However, it must be noted that the auditor would still need to obtain any applicable state licenses relating to the sale of pharmaceuticals. Rather than arranging for a direct shipment to the co-op, the auditor could alternatively arrange for direct shipment of an appropriate quantity of pharmaceuticals to either each retail pharmacy or each nursing home. That is, if buyers co-op 206 placed an order for 1,000 pills of Paxil, 150 of those pills being destined for retail pharmacy 200 (from which 50 pills and 100 pills are to go to nursing homes 210 and 212 respectively), 300 of those pills being destined for retail pharmacy 202 (from which 100 pills each are to go to nursing homes 214, 216, and 218), and 550 pills being destined for retail pharmacy 204 (from which 300 pills and 250 pills are to go to nursing homes 220 and 222 respectively), the auditor can arrange for shipment of 150 pills to retail pharmacy 200, 300 pills to retail pharmacy 202, and 550 pills to retail pharmacy 204. Alternatively, the auditor can arrange for the shipment of 50, 100, 100, 100, 100, 300, and 250 pills to nursing homes 210, 212, 214, 216, 218, 220, and 222 respectively. Also, it must be pointed out that an auditor who already has proper DEA licensing can arrange for direct shipment (plant delivery) to itself.

Figure 6:
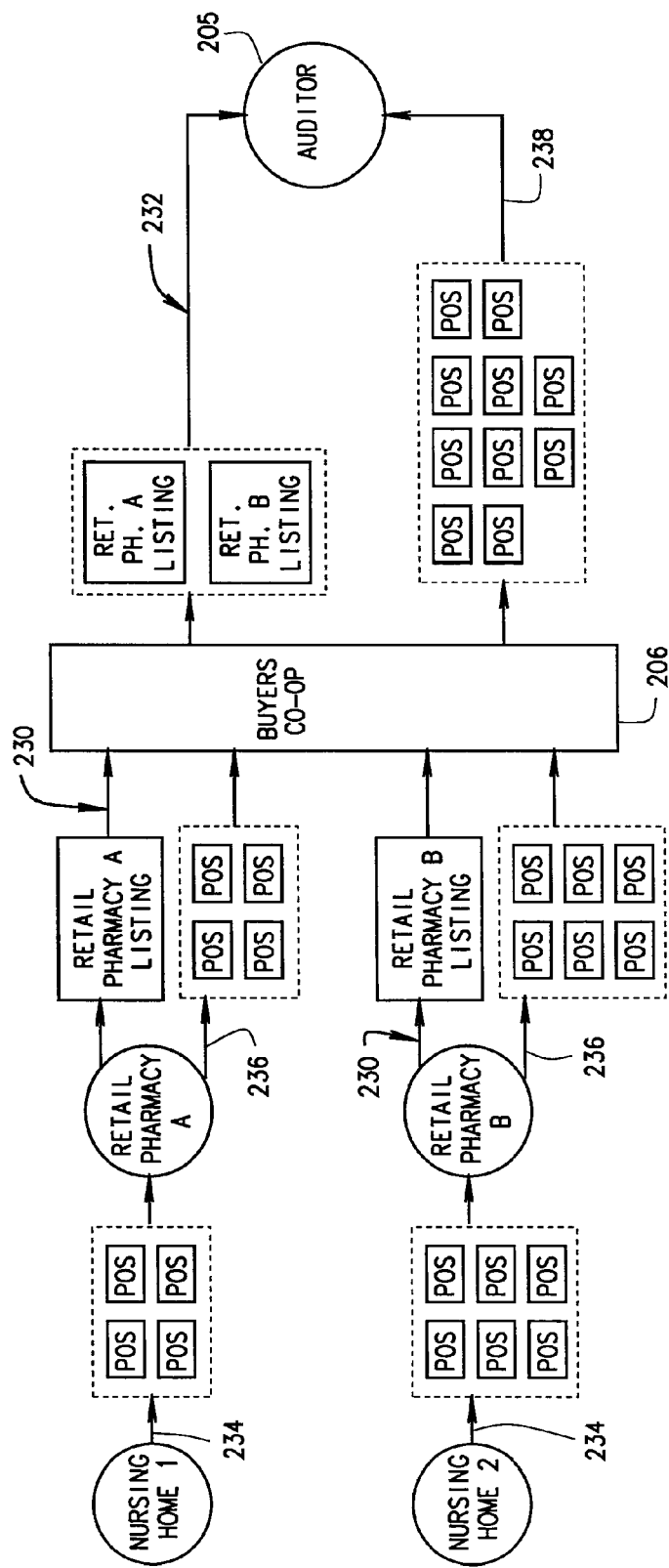
FIG. 6 depicts an example of the preferred flow of audit reports.

To perform the audit, information is needed that will reliably establish that the quantity of pharmaceuticals in the order are destined for a nursing home. Preferably, this information will be in the form of a report submitted by the buyers co-op. In the preferred embodiment of the present invention, this report is comprised of a listing compiled by each retail pharmacy that is requesting an amount of pharmaceuticals making up a part of the quantity of pharmaceuticals in the order. As previously discussed, each of these listings contains a record of pharmaceuticals supplied by that retail pharmacy to a nursing home. These listings can be generated from existing computerized records maintained by retail pharmacies. As shown in FIG. 5, each retail pharmacy 200, 202, and 204 will send a listing associated with the order to the buyers co-op 206. The buyers co-op 206 then forwards each of these listings on to the auditor. As shown in FIG. 6, which details the preferred flow of audit information to the auditor, the co-op 206 can either assemble each listing in path 232 into a master report (as identified by the box formed by dashed lines) that is forwarded to the auditor, or the co-op can individually forward each listing in path 232 to the auditor. Thus, when it is stated that an auditor receives a report, report refers to either a master report of each listing or report refers collectively to each individual listing received separately. Alternatively, each retail pharmacy can directly send an associated listing directly to the auditor. However, the preferable path of listings is depicted in FIGS. 5 and 6 along lines 230 (from each retail pharmacy to the buyers co-op) and 232 (from the buyers co-op to the auditor).

It is within the scope of the present invention to receive only the retail pharmacy listings (or for that matter only the POS or MAR), perform an audit thereon, and determine whether the co-op qualifies for purchasing the quantity of pharmaceuticals in the order at a discount solely on the basis of the retail pharmacy listings. However, to improve reliability of the status of determination as to whether the buyer qualifies for an "own use" discount, a second report containing additional audit information is preferably received. This additional audit information is preferably in the form of a POS for each of the patients in each nursing home supplied by each retail pharmacy requesting an amount of pharmaceuticals in the subject order.

Each nursing home, when placing a request for pharmaceuticals with its retail pharmacy supplier will also forward a copy of a POS for each patient in the nursing home needing the pharmaceutical identified in the request. These POSs should be sufficient to verify that the nursing home does in fact have patients who collectively need the requested amount of pharmaceuticals. The retail pharmacy, when forwarding this request for an amount of pharmaceuticals on to the buyers co-op, will also forward each of the applicable POSs (as shown in FIG. 6). Upon assembling its master order and placing it with the auditor, the co-op will also send each POS in its possession that is associated with the order. Alternatively, each nursing home or each retail pharmacy can forward the POS's directly to the auditor. However, the preferable path for the POS's is depicted in FIGS. 5 and 6 along lines 234 (from each nursing home to its retail pharmacy supplier), 236 (from each retail pharmacy to the buyers co-op), and 238 (from the buyers co-op to the auditor).

Once in receipt of an order for a quantity of a given type of pharmaceutical and each of the applicable listings and POSs, an audit can be performed on the order to determine whether the buyer qualifies for purchasing the desired quantity at a price reduced by an "own use" discount. There are two primary purposes for the audit. First, the audit seeks to compare the order with each applicable listing and POS to determine whether the quantity of pharmaceuticals in the order sufficiently matches a sum of the amounts requested by retail pharmacies on behalf of their nursing home customers as evidenced by the applicable listings and POSs. An exact one-to-one match between the order quantity and requested amounts, while preferable, is not necessary. A tolerance can be provided for discrepancies between the order quantity and listing/POS amounts. For example, a discrepancy could exist when an amount requested by a nursing home does not match a package amount offered by the pharmaceutical seller. That is, when a nursing home requests 85 pills of Prozac on behalf of its patients, but the pharmaceutical seller only sells Prozac in package amounts of 50 pills and 100 pills, the retail pharmacy or buyers co-op may upwardly adjust its order to match the 100 pill package offered by the seller. In such a case, a comparison between the order quantity and amounts evidenced in either the retail pharmacy listings or POSs may show a 15 pill discrepancy. By allowing for a tolerance in a comparison, such discrepancies need not adversely affect the status determination as to whether the buyer qualifies for an "own use" discount. However, the auditor can make note of such discrepancy and attribute a percentage size match resulting from the comparison. The percentage size match can be expressed as:

$$\% \text{ size match} = \frac{\text{Sum of pharmaceutical amounts identified in audit information}}{\text{Quantity of pharmaceuticals requested in order}}$$

In the case of 15 pills of a 100 pill order being unaccounted for, the percentage size match would be 85%.

The present invention allows the auditor to flexibly adjust an order if the size match is deemed to be too low. To determine the sufficiency of a size match, the usage history and "stand-by" requirements for the nursing home can be calculated. For example, the prescription pharmaceuticals that are supplied to nursing homes follow a monthly "fill" and "administer" protocol. The auditor will typically determine and place orders on a monthly basis for patients that are expected to consume the ordered pharmaceuticals during the targeted month (the monthly amount of needed pharmaceuticals being determined from the retail pharmacy listings, POSs, or MARs). This order is a snapshot of the nursing home's population at a particular point in time. The dynamics that this "snapshot" cannot reveal are the patient admissions and patient discharges that are occurring from day to day during the month.

Armed with a stack of "snapshots" (for previous monthly orders from the nursing homes), the auditor has the historical basis for determining the effect that these two dynamics (admissions and discharges) have on utilization and in particular "stand-by" requirements. Using these historical records, the auditor can determine, on average, how many new patients that a nursing home can expect each month, and, on average, how much and what kind of pharmaceuticals these patients will need. "Stand-by requirements" are the amounts of pharmaceuticals that a nursing home must have on hand to meet the pharmaceutical demands of newly admitted patients, and these requirements should also be factored into the consideration of whether a size match is sufficient. When it is said that the nursing home must have enough "stand-by" pharmaceuticals to immediately meet the needs of new patients, this means that the nursing home's retail pharmacy supplier also must have those pharmaceuticals standing by. Therefore, the stand-by requirement can be said to exist for either the nursing home or the retail pharmacy. In addition to the newly admitted patient dynamic, another factor that will affect a nursing home's stand-by requirements are the laws of the state in which the nursing home resides. If the nursing home operates in a state that allows the pharmaceuticals of deceased residents to be returned to the pharmacy, this will need to be factored into the stand-by calculation, and the auditor can identify those nursing homes and pharmacies that recycle. It should also be noted whether the nursing home allows discharged patients to take the monthly remainder of the pharmaceutical prescriptions home with them.

The concept of stand-by requirements is mainly focused on the new admission to the nursing home. This newly admitted patient must immediately have their prescription medication packaged in a "unit dose" system. A "unit dose" system is a system followed by nursing homes where the pharmaceuticals are individually packaged in a monthly supply or a partial monthly supply. All of the pharmaceuticals required by the newly admitted patients, be it for one day or 29 days of the remaining month, comprise the pharmacy's stand-by requirements. A tolerance can be set so that these requirements can be met with discounted pharmaceuticals as much as possible. When a size match is less than 15% for an order, the order can be audited for stand-by requirements and subsequently approved, as adjusted by the auditor.

Second, the audit seeks to trace the quantity of pharmaceuticals in the order to an institution eligible for an "own use" discount. Essentially, the audit compares the order with the retail pharmacy listings and POSs to determine whether patients in nursing homes need the quantity of pharmaceuticals ordered. This tracing can be done by identifying the nursing homes named in each retail pharmacy listing. A list of nursing homes whose requests are part of the order can be generated in a status report indicating the outcome of the audit.

Preferably, a more rigorous tracing is done. If each nursing home, when requesting pharmaceuticals from its retail pharmacy supplier, identifies the patients who are to receive those pharmaceuticals, each retail pharmacy can forward this patient information to the buyers co-op along with their pharmaceutical requests. In amassing its master order for a quantity of a given type of pharmaceutical, the buyers co-op can also identify the patients covered by its order. Thereafter, the patient information found in the order can be compared to the patients identified in each retail pharmacy listing and each POS. Once again, while it is preferable that an exact one-to-one match exists between the patients identified in the order and the patients identified in the audit information, a tolerance can exist. For example, a discrepancy in a patient match may exist because of human error in forwarding patient information or because of a loss of records for a patient (such as may occur if a patient in a nursing home dies). The auditor can make note of such discrepancies by attributing a percentage patient match resulting from the comparison. This percentage patient match can be expressed as:

$$\% \text{ Patient Match} = \frac{\text{\# of patients identified in audit information matching the patients in the order}}{\text{\# of patients in the order}}$$

If the difference between the number of patients in the order and the number of patients in the audit report varies by 10% or less, the patient match will be deemed to have sufficient correlation (nursing homes, on the average, discharge and admit 10% of their patient population each month). If the patient match is less than 90%, the auditor can calculate the stand-by requirements as previously discussed, adjust the order to fit within the stand-by tolerance, and certify the order as adjusted. If the patient match is 90% or higher, and the sum of the amounts attributed to each patient sufficiently matches the quantity of pharmaceuticals in an order, the audit will determine that a sufficient correlation exists between the order and audit reports. In such cases where the audit report supports either the order or an adjusted order, a status determination can be made that the buyer does in fact qualify for an "own use" discount.

The auditor preferably places the order with a pharmaceutical seller 208 if the audit results in a status determination that the buyer qualifies for purchasing the quantity of pharmaceuticals in the order at a price reduced by an "own use" discount. Pharmaceutical seller 208 may also desire a copy of a status report generated during the audit to further verify for itself that the buyer qualifies for an "own use" discount. In such situations, the auditor can either send a copy of the status report to the seller, or can make the status report available to the seller, such as by posting it on a secure web site.

Figure 7:
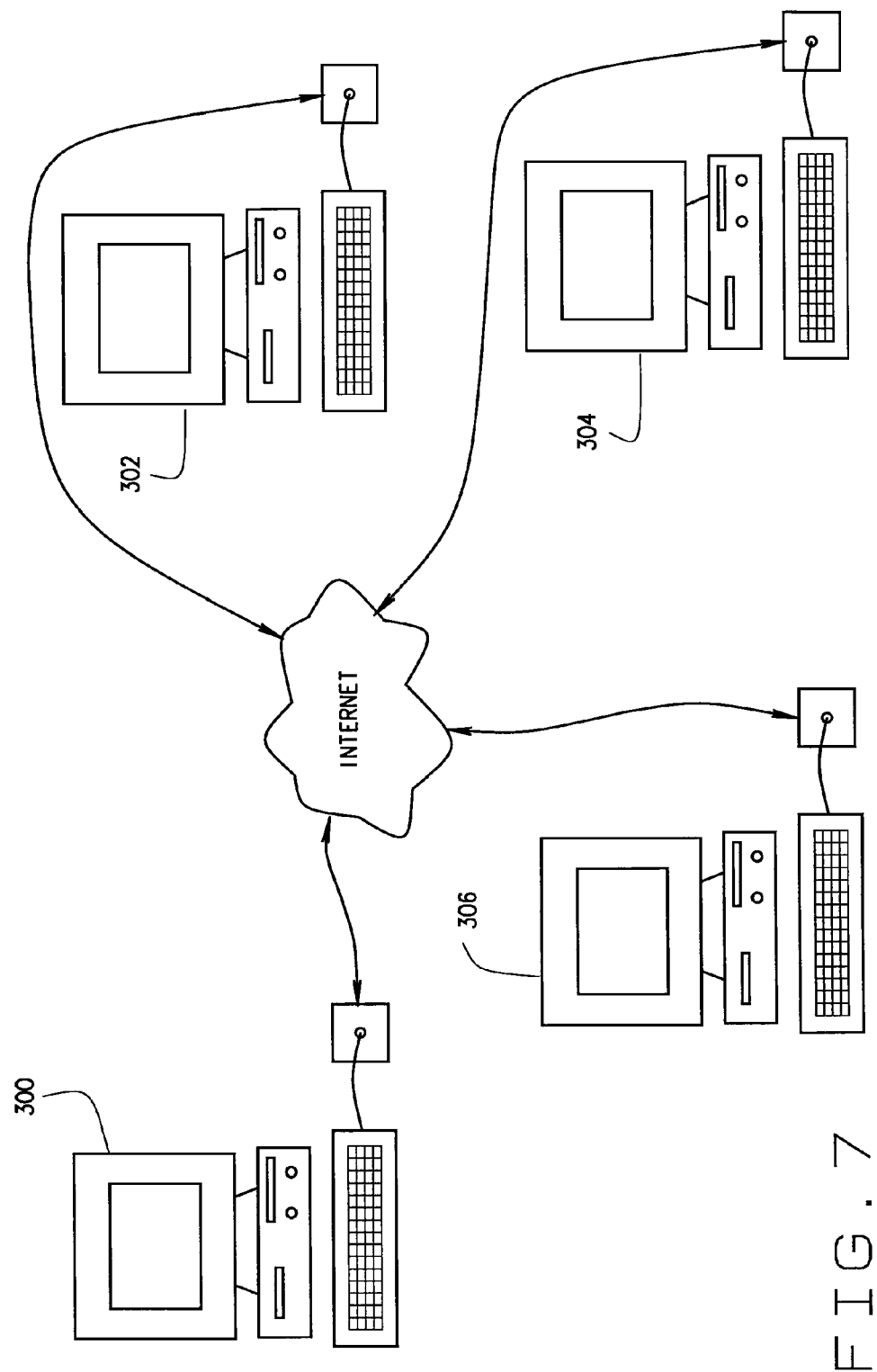
FIG. 7 is an overview of how computers operated by the auditor, buyers co-op, retail pharmacy, and nursing home can be connected to practice the present invention.

Preferably, the present invention is implemented on a computer system configured to function as a pharmaceutical order auditing system. FIG. 7 provides an overview of how computers used by the auditor, buyers co-op, retail pharmacies, and nursing homes can be set up to communicate with each other. The auditor uses computer 300 which is connected to the Internet in some fashion, either by a conventional phone line, a wireless connection, DSL, or the like. Buyer's co-op computer 302, retail pharmacy computer 304, and nursing home computer 306 can be similarly connected to the Internet. Each of these computers, which comprise a processor and associated memory for storing and executing software programs, can then communicate with each other using standard Internet communication methods.

Preferably, the auditor will maintain a web site that is accessible by persons seeking to place an order for "own use" discount pharmaceuticals. A page on the auditor's web site can offer an order sheet in which the buyer must provide data such as the type of pharmaceutical to be ordered, and the desired quantity of that type of pharmaceutical. As previously discussed, the order data would also preferably include a list of the patients who collectively need the quantity so entered. The buyer would then submit this order to the auditor as a transmission over the Internet. Alternatively, the auditor can receive orders by fax, phone, mail, e-mail, or the like. In such situations, the auditor can take such orders and manually enter the pertinent data thereon into the auditor's computer.

Thereafter, the buyers co-op would be requested to upload computer files containing the audit data. As previously discussed, this audit data can be gathered from the retail pharmacy listings maintained in the computerized records of retail pharmacies and from the POSs or MARs maintained by nursing homes.

While POSs and MARs are typically paper documents having handwriting thereon, the information contained on them is often entered into a computer by either nursing home personnel or a third party that performs data entry on behalf of the nursing home. Thus, a computerized record of the information found in the POS or MAR is usually available, and these computerized records can be transmitted to the auditor. If not, the auditor can obtain the hard copies of the POS or MAR and enter the data contained therein itself.

As for the retail pharmacy listings, it must be noted that retail pharmacies utilize various software packages to maintain those records (at least 20 different software packages are available). As a result, the computerized records maintained by the retail pharmacies will often be stored in computer files having differing data formats. Thus, for the auditing software to be able to read the data contained in these computer files, a conversion program (or a series of conversion programs) may have to be run to convert the retail pharmacy computer files to a common format. These conversions can also be run on the POS or MAR data if necessary. Such conversion programs are easily created by programmers of ordinary skill in the art and can be readily available. For example, web-based Computer-Talk Associates, Inc. of Blue Bell, Pa. discloses a list of forty-nine software development firms that specialize in management software solutions for retail pharmacies and the related pharmaceutical industry (see http://www.computer-talk.com).

Figure 8:
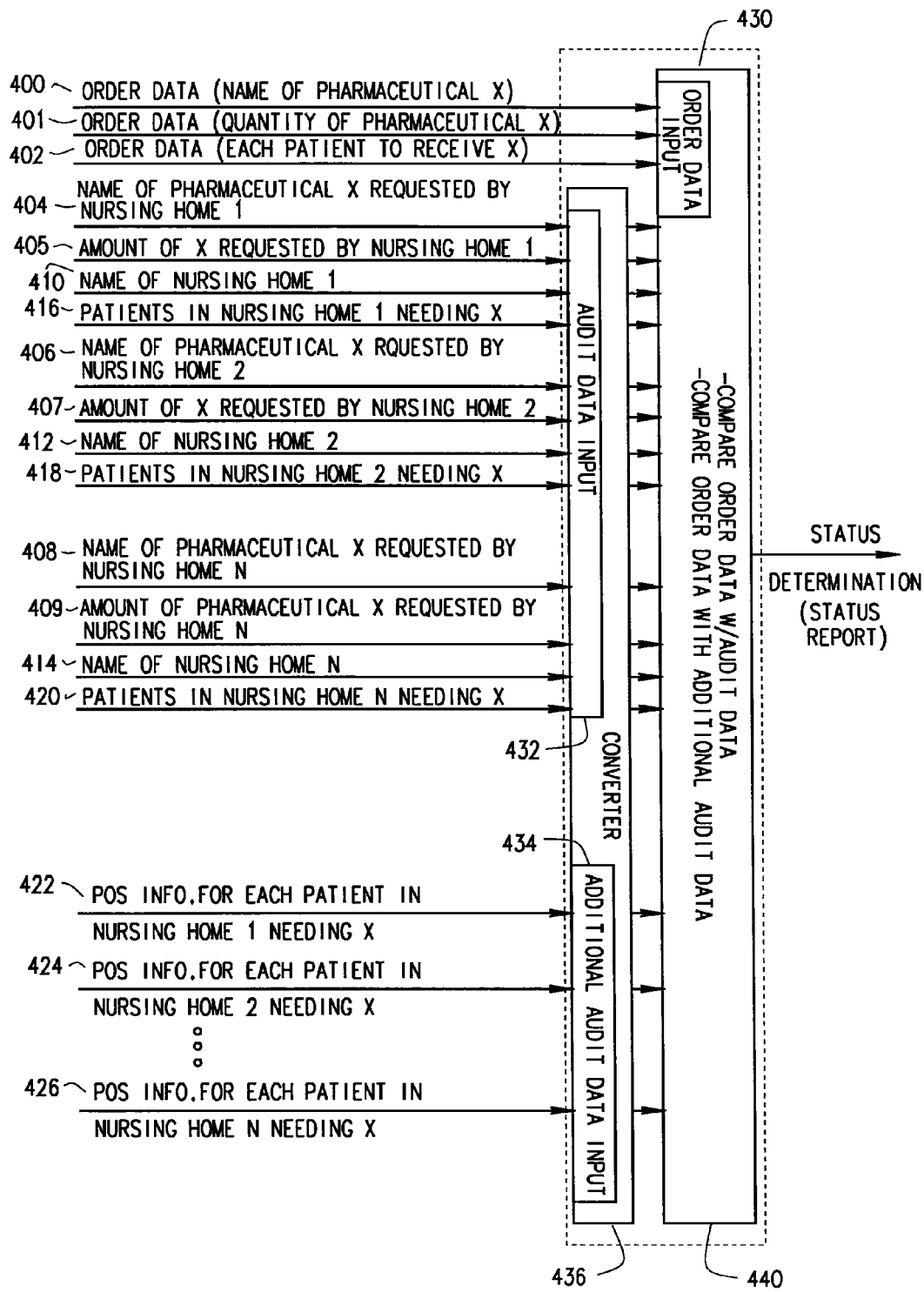
FIG. 8 is a flowchart depicting the flow of data and software functions of the present invention.

Once the auditor's computer has received the order data from the buyer, and all of the audit data has been converted to a common data format that is readable by the auditor's computer, a computerized audit can be performed. FIG. 8 depicts how software on the auditor's computer can be perform the audit. Order data, indicated by lines 400, 401, and 402 is received by the computer via a first input 430. Line 400 identifies the type of pharmaceutical ordered, line 401 identifies the quantity of that type of pharmaceutical ordered, and line 402 identifies each patient needing a portion of the stated quantity. The information found in the audit reports is received by the computer via second input 432 and third input 434. Converter 436 converts the audit data to a common format. It also must be pointed out that the conversion process is unnecessary if the audit data already shares a common format. It must be noted that the first input 430, second input 432 and third input 434 can be separate inputs to the auditor's computer or can be the same physical input port. The notations first, second and third are used for clarity to delineate the three forms of data that are needed by the audit computer. It must be further noted that in describing the auditor's computer system, the term "computer" can encompass more than just a single computer, and may encompass a plurality of computers that are connected in a network.

Preferably input 432 receives the audit data gathered from the report comprised of each listing compiled by each retail pharmacy requesting an amount of "own use" discount pharmaceuticals. Lines 404, 406, and 408 identify the type of pharmaceutical requested by each retail pharmacy. Lines 405, 407, and 409 identify the amounts of that type of pharmaceutical requested by each retail pharmacy. Lines 410, 412, and 414 identify the names of the nursing homes making the request, and lines 416, 418, and 420 identify the patients who collectively need the amounts requested.

As previously stated, the audit can be performed without the patient data, however, this data is preferably included to improve the reliability of the audit. Having received the order data and the retail pharmacy listing data, software 440 on the auditor's computer can perform an audit on the order by comparing the order data with the audit data. The software can compare the type of pharmaceutical in the order data with the type of pharmaceutical in the audit data to verify that there is a type match between the order data and the audit data. Thereafter, the software can compare the order quantity with the sum of each amount identified in the audit data for a type of pharmaceutical that matches the order type. As previously explained, an exact one-to-one match between the order quantity and requested amounts, while preferable, is not necessary. A tolerance can be provided for discrepancies between the order quantity and listing amounts, such, as when amounts requested by a nursing home do not match a package amount offered by the pharmaceutical seller, or when the discrepancy fits within a nursing home's stand-by requirements. The auditing software can make note of any discrepancies and attribute a percentage size match resulting from the comparison.

Next, the software can compare the patients identified in the order data with the patients identified in the audit data to verify that there is a patient match between the order data and the audit data. As previously discussed, the patient data also need not be an exact one-to-one match, although it would be preferable. In such cases, the software can attribute a percentage patient match to the comparison.

If the software determines that there is a type match, a sufficient size match, and a sufficient patient match, the software can produce a status report indicating that a status determination has been made verifying that the buyer does in fact qualify for purchasing the quantity of pharmaceuticals in the order at a price reduced by an "own use" discount. Of course, if the software determines that there is not a type match, a sufficient size match, or a sufficient patient match, the status report can indicate that a status determination has been made that the buyer does not qualify for the discount based on the original order. However, the software can also calculate an "adjusted order" that is supported by the audit data. The software can downwardly adjust the order until there is a sufficient size match and a sufficient patient match. Alternatively, the software can utilize the usage history of the nursing home to calculate the nursing home's stand-by requirements, and then downwardly adjust the order so that the quantity requested in the adjusted order is the actual amount of pharmaceuticals specifically identified in the audit data plus the calculated stand-by requirement. Thereafter, the software can make a status determination on the basis of the adjusted order.

However, before making its status determination, the auditor's computer preferably receives additional audit data via input 434. As previously discussed, this additional audit data is preferably gathered from a report comprised of each POS for each pertinent patient in each nursing home that receives its pharmaceuticals from one of the retail pharmacies making a request for amount of pharmaceuticals. The additional audit data on lines 422, 424, and 426 can identify all or any combination of the following: the type of pharmaceuticals needed by each patient, the amounts of that type of pharmaceutical needed by each patient, and the names of each patient needing that type of pharmaceutical.

The software 440 can then run the same comparison previously discussed against the additional audit data, wherein the order data is compared to the additional audit data. If there is a type match, a sufficient size match, and a sufficient patient match resulting from the two comparisons, the software can produce a status report indicating that a status determination has been made verifying that the buyer does in fact qualify for purchasing the quantity of pharmaceuticals in the order at a price reduced by an "own use" discount. If the matches are insufficient, the software can adjust the order as previously discussed. It must be noted that the software can perform the audit by comparing the additional audit data with the audit data rather than the order data. In such a case, the audit data would be compared with the order data to check whether the audit data supports the order data, and the additional audit data would be compared with the original audit data to check whether the additional audit data supports the original audit data. If the additional audit data supports the original audit data, a conclusion can be drawn as to whether the additional audit data supports the order data (depending upon the results of a comparison between the order data with the original audit data).

Figure 9:
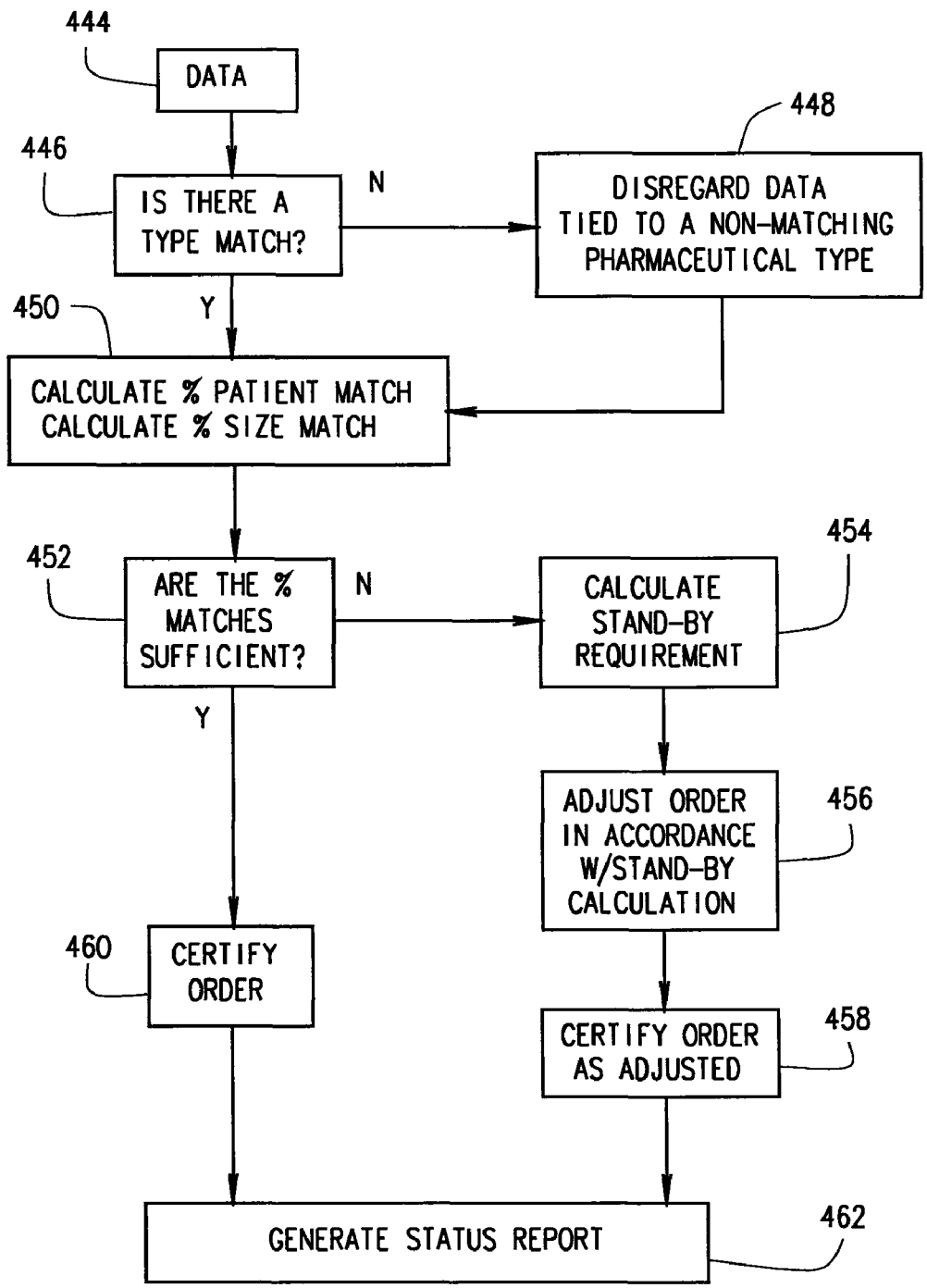
FIG. 9 is a flowchart depicting the operation of the software of the present invention.

FIG. 9 is a flowchart depicting how the software 440 can be configured to perform its comparison between the order data and the audit data. In FIG. 9, box 444 represents the order data and audit data received by the pharmaceutical order auditing system. At box 446, the software determines whether there is a type match between the order data and the audit data. If a discrepancy exists between the type of pharmaceutical ordered and those identified in the audit data, the software, at box 448, will disregard any audit data that is tied to a type of pharmaceutical that does not match the order in making subsequent calculations. Thereafter, at box 450, the software calculates the percentage patient match and the percentage size match. Then, at box 452, the software determines whether the percentage matches are sufficient. As previously discussed, the preferable sufficiency parameters are 85% for the size match and 90% for the patient match. However, these parameters can be varied as desired by the auditor, keeping in mind that if the bar is set too low, then the pharmaceutical seller may be unwilling to provide the discount. If both percentage matches are sufficient, then the software proceeds to box 460 where the order is deemed certified. If either of the percentage matches are insufficient, the software proceeds to box 454 where the stand-by requirement is calculated. Here, the software can look to stored data representing orders and audit information submitted by the buyer in previous months. From this historical data, the software can estimate how much pharmaceuticals are needed on average to supply patients that are expected to be new admissions during the month. Thereafter, at box 456, the software can downwardly adjust the order so that there is a 100% size match. Then, the software can upwardly adjust the fully matching order by the calculated stand-by requirement to create an adjusted order that fits within a stand-by tolerance. Thereafter, the software can certify the order as adjusted at box 458. After the order, or adjusted order, has been certified, the software can generate a status report at box 462.

Figure 10:
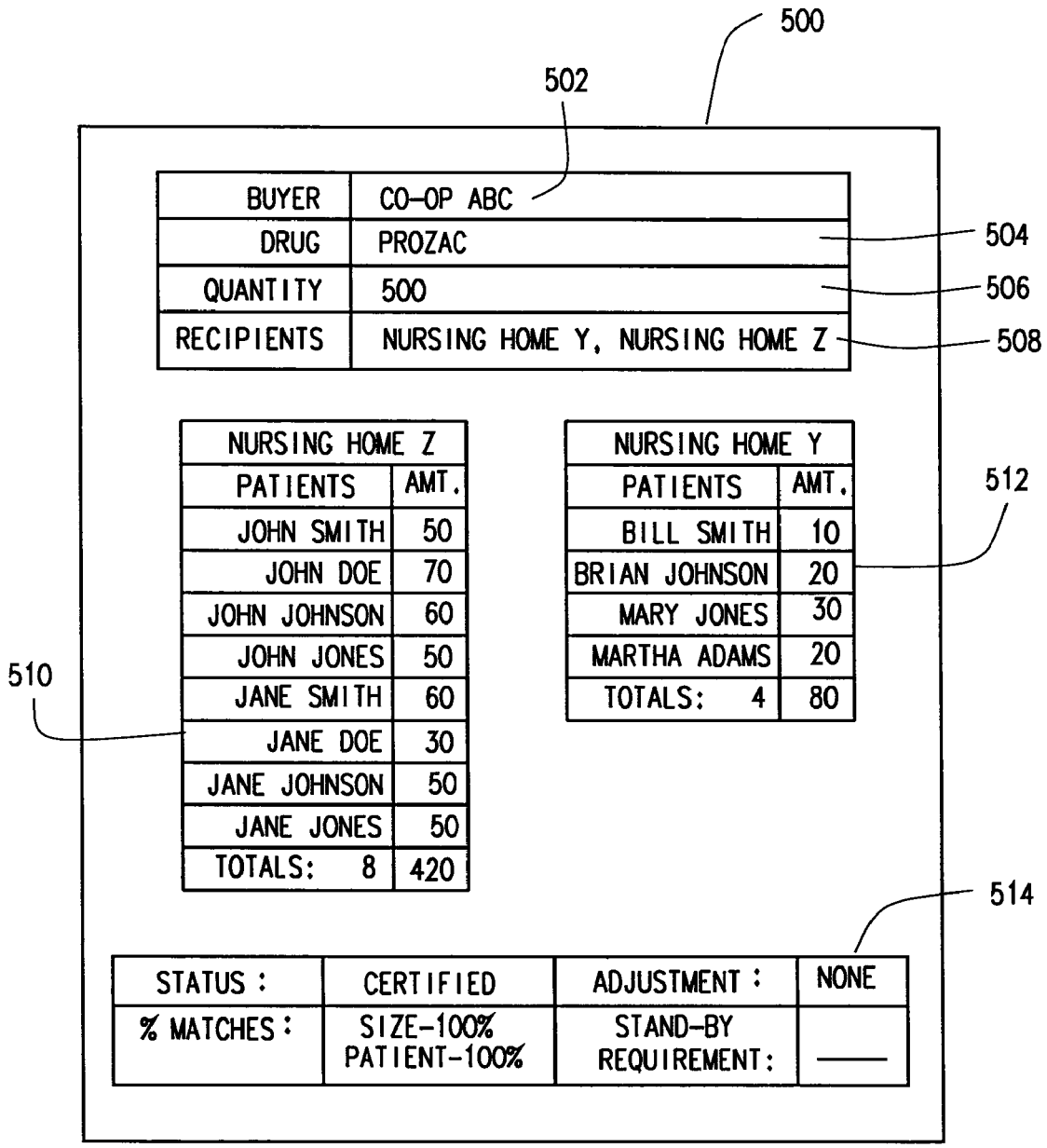
FIG. 10 is an example of a status report that can be generated with the present invention.

FIG. 10 depicts a status report that can be generated by the above-described software. Status report 500 identifies the buyer in box 502, the type of pharmaceutical ordered in box 504, the quantity of that type of pharmaceutical ordered in box 506, and the nursing home recipients of the order in box 508. Also included is a box 514 identifying the status determination that has been made. This status determination can be either "certified" or "certified as adjusted". Preferably, the status determination box 514 also identifies the percentage matches in terms of size match and patient match found during the audit. In cases where the order is "certified as adjusted", the status report can identify the calculated standby requirement and identify the amount of adjustment. Also, in cases where a pharmaceutical seller wants to decide for itself, on the basis of the percentage matches, whether there is sufficient support for the order to justify a discount, the status determination box may solely identify the percentage matches rather than making a "certified" or "certified as adjusted" notation. Also, the status report 500 can be fully itemized by showing patient lists 510 and 512 that identify each patient receiving an amount of pharmaceuticals that makes up the order.

As previously discussed, the auditor can send this status report to the pharmaceutical seller along with the co-op's order to demonstrate to the seller that the co-op does in fact qualify for an "own use" discount. Alternatively, the auditor can make this report available to the seller should the seller want to review it, for example by posting the report on a web site accessible by the pharmaceutical seller. One can also practice the present invention by acting as a data gatherer who obtains the proper audit information (retail pharmacy listings, POSs, MARs, etc.) and forwards the audit information on to a pharmaceutical seller. Rather than performing the comparison between the audit information and order information itself, one can place the order for a quantity of pharmaceuticals and forward pertinent audit information on to the seller, who can then perform an audit on the order itself. If the pharmaceutical seller determines that the forwarded audit information sufficiently supports the order, the pharmaceutical seller will provide the discount. Alternatively, rather than actually forwarding the audit information to the seller, the audit information can be posted on a website accessible to pharmaceutical sellers. Before providing a discount, the pharmaceutical seller can access this webpage to examine the posted audit information. If the pharmaceutical seller determines that the audit information sufficiently supports the order, it can provide the discount.

While the present invention has been described by reference to the above-discussed embodiments, it should be understood and apparent to those skilled in the art that modifications and variations of the invention may be constructed without departing from the scope of the invention. It is therefore intended that the invention be limited only by the scope of the claims appended hereto, and their legal equivalents.

What is claimed is:

1. A computer-implemented method for auditing data relating to pharmaceuticals, the method comprising:
   receiving first data, the first data comprising data representative of a first quantity of pharmaceuticals desired by a retail pharmacy on behalf of another entity, wherein the retail pharmacy is not eligible for an "own use" discount when purchasing pharmaceuticals for its own use;
   receiving second data, the second data comprising (1) data representative of the another entity, and (2) data representative of a second quantity of pharmaceuticals needed for use by the another entity; and
   processing the first data against the second data, wherein the processing step comprises (1) determining whether the another entity is an entity whose purchase of pharmaceuticals for its own use is eligible for the "own use" discount, and (2) in response to a determination that the another entity is an entity whose purchase of pharmaceuticals is eligible for the "own use" discount, (a) determining whether the first quantity matches the second quantity within a pre-determined tolerance, and (b) in response to a determination that the first quantity matches the second quantity within the predetermined tolerance, identifying the first quantity as eligible for an "own use" purchase discount; and
   wherein the method steps are performed by a processor in response to executing a software program.

2. The method of claim 1 wherein the another entity data comprises data representative of a nursing home.

3. The method of claim 2 wherein the pre-determined tolerance comprises a first pre-determined tolerance, wherein the nursing home has a plurality of patients residing therein, wherein the first data further comprises data representative of a first number of patients who are to receive the first quantity of pharmaceuticals, wherein the second data further comprises data representative of a second number of patients in said nursing home who need the second quantity of pharmaceuticals, and wherein the processing step further comprises:
   the processor (1) determining whether the first number of patients matches the second number of patients within a second pre-determined tolerance, and (2) further conditioning the identifying step on it being determined that the first number of patients matches the second number of patients within the second pre-determined tolerance.

4. The method of claim 2 wherein the first data further comprises data representative of a type of the first quantity of pharmaceuticals, wherein the second data further comprises data representative of a type of the second quantity of pharmaceuticals, and wherein the processing step further comprises:
   the processor (1) determining whether a type match exists between the type of the first quantity of pharmaceuticals and the type of the second quantity of pharmaceuticals, and (2) further conditioning the identifying step on a type match being determined to exist.

5. The method of claim 1 further comprising:
   in response to the identifying step, placing a purchase request for the first quantity of pharmaceuticals with a pharmaceutical supplier at a price reduced by the "own use" discount.

6. The method of claim 1 further comprising:
   the processor generating a status report, the status report including a result from the processing step.

7. The method of claim 1 further comprising:
   maintaining a website;
   wherein the first data receiving step comprises receiving the first data as an input through the website; and
   wherein the second data receiving step comprises receiving the second data as an input through the website.

8. The method of claim 1 wherein the second data comprises data derived from at least one member of the group consisting of a retail pharmacy listing, a medication administration record (MAR), and a physician's order sheet (POS).

9. The method of claim 1 further comprising the following steps performed by the processor:
   in response to a determination that the first quantity does not match the second quantity within the predetermined tolerance, (1) downwardly adjusting the first quantity to a new quantity such that the new quantity matches the second quantity within the predetermined tolerance, and (2) identifying the new quantity of the pharmaceuticals as eligible for an "own use" purchase discount.

10. An apparatus for auditing data relating to pharmaceuticals, the apparatus comprising:

a processor and associated memory configured to:
receive first data, the first data comprising data representative of a first quantity of pharmaceuticals desired by a retail pharmacy on behalf of another entity, wherein the retail pharmacy is not eligible for an "own use" discount when purchasing pharmaceuticals for its own use;
receive second data, the second data comprising (1) data representative of the another entity, and (2) data representative of a second quantity of pharmaceuticals needed for use by the another entity; and
perform a processing operation on the first data and the second data, wherein the processing operation is defined via a plurality of software instructions for execution by the processor that are configured to (1) determine whether the another entity is an entity whose purchase of pharmaceuticals for its own use is eligible for the "own use" discount, and (2) in response to a determination that the another entity is an entity whose purchase of pharmaceuticals is eligible for the "own use" discount, (a) determine whether the first quantity matches the second quantity within a pre-determined tolerance, and (b) in response to a determination that the first quantity matches the second quantity within the predetermined tolerance, identify the first quantity as eligible for an "own use" purchase discount.

11. The apparatus of claim 10 wherein the another entity data comprises data representative of a nursing home.

12. The apparatus of claim 11 wherein the pre-determined tolerance comprises a first pre-determined tolerance, wherein the nursing home has a plurality of patients residing therein, wherein the first data further comprises data representative of a first number of patients who are to receive the first quantity of pharmaceuticals, wherein the second data further comprises data representative of a second number of patients in said nursing home who need the second quantity of pharmaceuticals, and wherein the plurality of software instructions that define the processing operation are further configured to (1) determine whether the first number of patients matches the second number of patients within a second pre-determined tolerance, and (2) further condition the identification operation on it being determined that the first number of patients matches the second number of patients within the second pre-determined tolerance.

13. The apparatus of claim 11 wherein the first data further comprises data representative of a type of the first quantity of pharmaceuticals, wherein the second data further comprises data representative of a type of the second quantity of pharmaceuticals, and wherein the plurality of software instructions that define the processing operation are further configured to (1) determine whether a type match exists between the type of the first quantity of pharmaceuticals and the type of the second quantity of pharmaceuticals, and (2) further condition the identification operation on a type match being determined to exist.

14. The apparatus of claim 10 wherein the processor and associated memory are further configured to, in response to the identification operation, place a purchase request for the first quantity of pharmaceuticals with a pharmaceutical supplier at a price reduced by the "own use" discount.

15. The apparatus of claim 10 wherein the processor and associated memory are further configured to generate a status report, the status report including a result from the processing operation.

16. The apparatus of claim 10 further comprising:
a website, wherein the processor and associated memory are configured to receive the first data and the second data as inputs via the website.

17. The apparatus of claim 10 wherein the second data comprises data derived from at least one member of the group consisting of a retail pharmacy listing, a medication administration record (MAR), and a physician's order sheet (POS).

18. The apparatus of claim 10 wherein the plurality of software instructions that define the processing operation are further configured to:
in response to a determination that the first quantity does not match the second quantity within the predetermined tolerance, (1) downwardly adjust the first quantity to a new quantity such that the new quantity matches the second quantity within the predetermined tolerance, and (2) identify the new quantity of the pharmaceuticals as eligible for an "own use" purchase discount.

19. A computer program product for auditing a pharmaceutical purchase request, the computer program product comprising: a plurality of software instructions, that are executable by a processor and resident on a processor-readable storage medium, for (1) receiving first data, the first data comprising data representative of a first quantity of pharmaceuticals desired by a retail pharmacy on behalf of another entity, wherein the retail pharmacy is not eligible for an "own use" discount when purchasing pharmaceuticals for its own use, (2) receiving second data, the second data comprising (a) data representative of the another entity, and (b) data representative of a second quantity of pharmaceuticals needed for use by the another entity, and (3) processing the first data against the second data, wherein the processing comprises (a) determining whether the another entity is an entity whose purchase of pharmaceuticals for its own use is eligible for the "own use" discount, and (b) in response to a determination that the another entity is an entity whose purchase of pharmaceuticals is eligible for the "own use" discount, (i) determining whether the first quantity matches the second quantity within a pre-determined tolerance, and (ii) in response to a determination that the first quantity matches the second quantity within the predetermined tolerance, identifying the first quantity as eligible for an "own use" purchase discount.

20. The computer program product of claim 19 wherein the software instructions further comprise a plurality of software instructions that are executable by the processor and resident on the processor-readable storage medium for, in response to a determination that the first quantity does not match the second quantity within the predetermined tolerance, (1) downwardly adjusting the first quantity to a new quantity such that the new quantity matches the second quantity within the predetermined tolerance, and (2) identifying the new quantity of the pharmaceuticals as eligible for an "own use" purchase discount.

* * * * *